United States Patent [19]

Tsikos

[11] 4,353,056
[45] Oct. 5, 1982

[54] CAPACITIVE FINGERPRINT SENSOR

[75] Inventor: Constantine Tsikos, Pennsauken, N.J.

[73] Assignee: Siemens Corporation, Iselin, N.J.

[21] Appl. No.: 156,571

[22] Filed: Jun. 5, 1980

[51] Int. Cl.³ .............................................. G06K 9/00
[52] U.S. Cl. ............................. 340/146.3 E; 361/283
[58] Field of Search .............. 340/146.3 E; 324/60 C, 324/61 R, 71 R; 361/271, 283, 328

[56] References Cited

U.S. PATENT DOCUMENTS

| 3,622,989 | 11/1971 | Dowdy | 340/146.3 E |
| 3,648,240 | 3/1972 | Jacoby et al. | 340/146.3 E |
| 3,781,855 | 12/1973 | Killen | 340/146.3 E |
| 3,865,488 | 2/1975 | Del Rio | 340/146.3 E |
| 3,993,888 | 11/1976 | Fellman | 340/146.3 E |
| 4,281,313 | 7/1981 | Boldridge | 340/146.3 SY |

OTHER PUBLICATIONS

Bevczy et al., "Transducer with a Sense of Touch" Tech. Support Package, J.P.L., Pasadena California, Nov. 1979.

Primary Examiner—Leo H. Boudreau
Attorney, Agent, or Firm—Karl F. Milde, Jr.

[57] ABSTRACT

The sensor incorporates a sensing member which has a sensing surface for receiving a fingerprint and sensing means for sensing the ridges and valleys of the skin of the finger under investigation. The sensing member contains a multitude of small capacitors. When the finger is pressed against the sensing surface, the capacitances of the capacitors are locally changed in accordance with the ridges and valleys. The information about the capacitance distribution is transformed into an electric signal.

4 Claims, 9 Drawing Figures

CAPACITIVE FINGERPRINT SENSOR

FIELD OF THE INVENTION

This invention relates to an apparatus for identification of fingerprints. In particular, this invention relates to an input transducer or input sensor for sensing a fingerprint in order to enter corresponding electrical information into a fingerprint identification device. Still more particularly, this invention relates to a fingerprint sensor having a surface for pressing a finger thereto and having means for reading the ridges and valleys of the finger when pressed against the sensing surface.

BACKGROUND OF THE INVENTION

In a fingerprint input transducer or sensor, the finger under investigation is usually pressed against a flat surface, such as one side of a glass plate, and the ridge-valley pattern of the finger tip is sensed by some sensing means such as an interrogating light beam. The processing of the fingerprint information thus obtained may comprise laser techniques.

Fingerprint identification devices of this nature are generally used to control the access of individuals to information (information access control), for instance, computer terminals, or to buildings (physical access control).

One of the problems associated with fingerprint sensors concerns the reliable and accurate transformation of the ridge-valley pattern of the finger tip into electrical signals. Optical techniques which are widely used require a high amount of sophisticated equipment. Simple electromechanical sensors are sometimes not sensitive enough.

Therefore, there is a need for a fingerprint input sensor or transducer which is adapted to reliably sense the fingerprint relief and transform the sensed information into electrical signals. The fingerprint sensor should be of simple structure.

BRIEF DESCRIPTION OF THE INVENTION

Objects

It is an object of the present invention to provide a fingerprint sensor or transducer of simple structure which is capable of detecting and sensing the information contained in the skin structure of a human finger, especially the finger tip, and which can deliver an electric output signal in accordance with the pattern of ridges and valleys of the finger.

It is another object of this invetion to provide a fingerprint sensor which works fast and which can be reused after an anteceding fingerprint investigation.

It is still another object of this invention to provide a fingerprint sensor wherein the fingerprint information can be stored for a certain period of time and read out or displayed thereafter, when desired.

It is still another object of this invention to provide a fingerprint sensor without use of electro-mechanical or optical techniques.

Summary

According to this invention, the fingerprint sensor contains a sensing member which has a sensing surface for receiving a fingerprint. The sensing surface is part of a sensing member which contains a large number of small capacitors. These capacitors are smaller than the width of the ridges and valleys of the finger tip in order to obtain a high resolution. The capacitors are arranged close to the sensing surface in a two dimensional array. When the finger is pressed against the sensing surface, the capacitance of the capacitors is locally changed according to the ridge/valley pattern of the finger. The change of capacitance can be detected by electrical means. Thus, a "capacitive fingerprint sensor" is obtained. This sensor can be used, for instance, for personal access control.

The foregoing and other objects, feature and advantages of the invention will be apparent from the following more particular description of the preferred embodiments of the invention, as illustrated in the accompanying drawings.

DETAILED DESCRIPTION OF THE PREFERRED EMBODIMENTS

Figure 1:
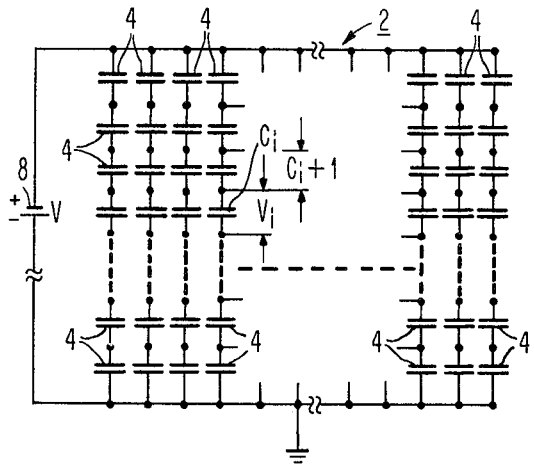
FIG. 1 is an electrical diagram of an array of capacitors in a sensing member, whereby several groups of capacitors are connected in series.

According to FIG. 1, the sensing member of a fingerprint sensor 2 contains a two-dimensional array of capacitors 4. The array is preferrably rectangular. Also other arrangements can be selected. FIG. 1 represents an enlarged portion of the sensing member. Therefore, it is to be understood that a great number of capacitors 4 are provided. The capacitors 4 are smaller than the ridges and valleys of the finger (not shown in FIG. 1) under investigation. The size of the capacitors 4 is at least by a factor 5 smaller than the average width of the ridges and valleys of the finger. All capacitors 4 are located in a plane which is parallel to the flat sensing surface (not shown in FIG. 1) of the fingerprint sensor 2. For the sake of illustration, it can be assumed that the sensing surface is parallel to the plane of the sheet and that the electrodes are also arranged parallel to the sensing surface.

In the embodiment of FIG. 1, there are indicated many groups of capacitors 4 which are connected in series. However, only seven series connections of capacitors 4 are shown in detail. The series connections are in turn connected in parallel to each other. They are supplied by a voltage source 8 having a voltage V. One of the capacitors 4, which is arbitrarily chosen, has the capacitance $C_i$ and the voltage $V_i$. If all capacitors 4 include the same dielectric material and if they all have the same size, their capacitance $C_i$ and their voltage $V_i$ will be all the same. This corresponds to a status of the fingerprint sensor where the finger is not pressed against the sensing surface. When the finger touches the surface, the voltage distribution in a series connection of capacitors 4 may change. The voltages $V_i$ of the capacitors 4 may be sensed by multiplexor techniques.

Figure 2:
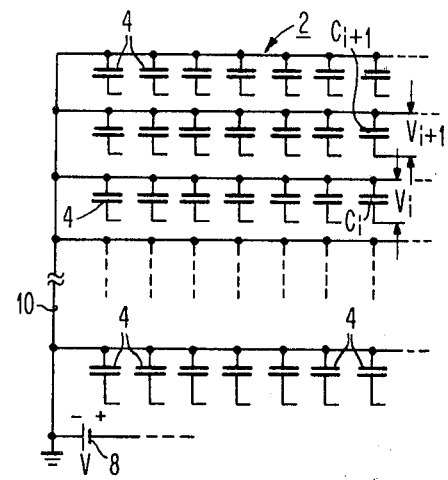
FIG. 2 is an electrical diagram of an array of sensing member capacitors, one electrode of each of which is connected to a common connection line.

In the embodiment of FIG. 2, there is also provided a large number of capacitors 4. Again an arbitrarily chosen capacitor 4 is assumed to have the capacitance $C_i$ and the voltage $V_i$. All capacitors 4 again are arranged in an rectangular array. Other configurations than such an array may also be chosen. One electrode of all capacitors 4 is here connected to a common connection line 10, which is connected to ground. Connected to ground is also the negative terminal of a voltage source 8 having the voltage V. The capacitors 4 can be charged up to the voltage +V either successively or simultaneously by some means not shown. As long as the finger under investigation does not touch the sensing surface, all capacitors 4 will have the same capacitance $C_i$ and the same voltage $V_i$. The individual voltage $V_i$ will change as soon as the finger is pressed against the sensing surface. As will be explained later, the voltage $V_i$ of the individual capacitors 4 can be detected in a multiplexing process.

It is well known that the capacitance C of a capacitor is determined by $$C = k \cdot (S/d), \qquad (1)$$

where C is the capacitance in Farads, k is the dielectric constant, S is the surface of the capacitor in square inches, and d is the distance between the electrodes of the capacitor in inches. It is also known that $$Q = C \cdot V, \qquad (2)$$

where Q is the charge in Coulombs, C is the capacitance in Farads, and V is the voltage.

From (1) it is obvious, that the capacitance C can be altered by changing the distance d and/or the dielectric constant k. The surface S of the capacitor is usually a fixed quantity. From (2) it is obvious that the capacitor voltage V will change when the capacitance C (and/or the charge Q) is changed.

In the embodiments of FIGS. 1 and 2, the distance d will be varied locally in accordance with the ridge/valley pattern of the finger. In other words, the capacitance of the capacitors 4 will be changed locally when the finger under investigation is pressed against the sensing surface. As a result, in FIG. 1 the voltage distribution in some or all series connections of capacitors 4 will be changed. In FIG. 2 some or all capacitors 4 will assume another voltage. The change of the voltage distributions and the voltage values, respectively, can be detected by electric detecting means which are described in more detail below.

Figure 3:
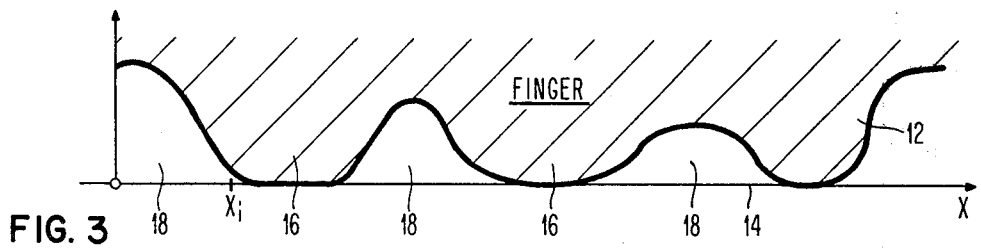
FIG. 3 is an enlarged cross section of a human finger showing ridges and valleys, the finger being pressed to a sensing surface and extending along an axis x.

According to FIG. 3, a finger 12 is pressed against a sensing surface 14 which extends in a direction x. The finger 12 has ridges 16 and valleys 18.

Figure 4:
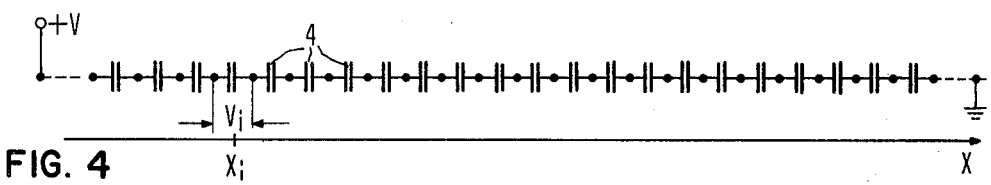
FIG. 4 is a one-dimensional array of capacitors connected in series to a voltage source for sensing the finger pattern shown in FIG. 3.

In FIG. 4 is illustrated a string of series connected capacitors 4. The string is supplied by a voltage V. As compared to FIG. 3, the size of the capacitors 4 is much smaller than the size of the ridges 16 and valleys 18 of the finger 12. It is assumed that the electrode plates of the capacitors 4 may be arranged parallel to the surface 14.

Figure 5:
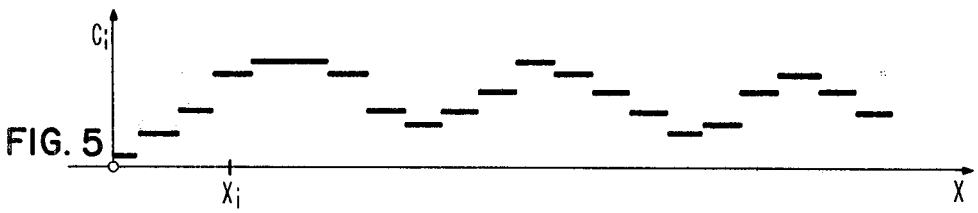
FIG. 5 is the distribution of capacitances of the capacitors shown in FIG. 4 under the effect of the pressing finger according to FIG. 3.

In places of the ridges 16, the electrodes of each capacitor 4 will approach each other. This will result in a higher capacitance according to (1). In places of the valleys 18 of the skin surface, however, the electrodes will not be pressed together so much, so that a smaller capacitance will be obtained. This can be seen in FIG. 5, where the distribution of capacitance $C_i(x)$ in direction x is illustrated.

Figure 6:
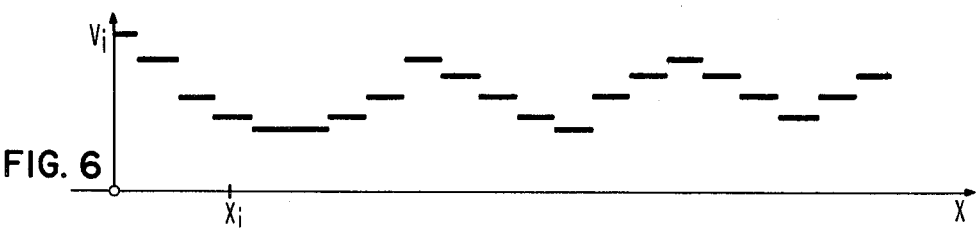
FIG. 6 is the distribution of the individual voltages of the capacitors shown in FIG. 4 under the effect of the pressing finger according to FIG. 3.

In FIG. 6 the voltage distribution $V_i(x)$ of the string of capacitors 4 in FIG. 4 is shown. As can be seen by comparison with FIG. 3, the voltage distribution $V_i(x)$ of the string of capacitors 4 corresponds to the pattern of ridges 16 and valleys 18 on the skin surface of the finger 12.

In other words, by placing the human finger on the sensing surface of a capacitive fingerprint sensor, the fingerprint modulates the capacitance and voltage chain.

Figure 7:
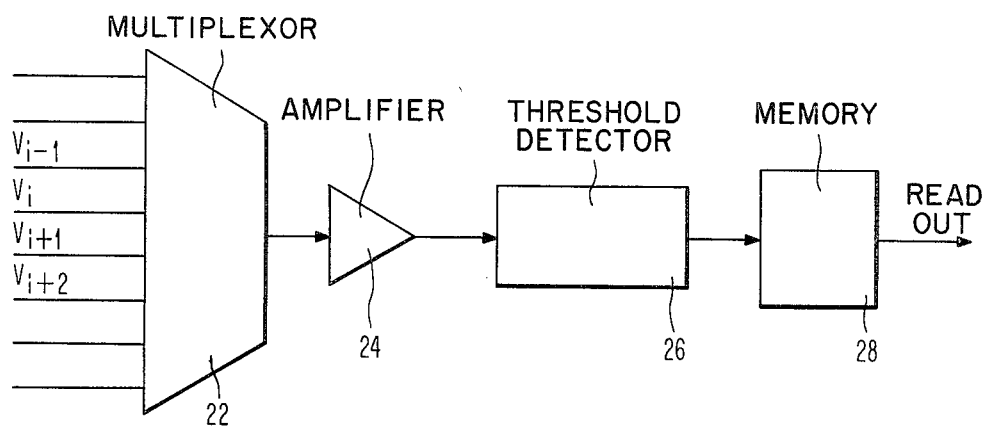
FIG. 7 is an electric circuit for reading and storing the individual voltages of the capacitors in arrays such as in FIGS. 1 and 2.

As illustrated by the reading and storage circuitry in FIG. 7, the individual voltages $V_i$, $V_{i+1}$... can be detected and processed by means of multiplexing techniques. For this purpose, a multiplexor 22 is provided the inputs of which are connected to the individual capacitors 4. The multiplexor successively connects the capacitors 4 to an amplifier 24, preferably a difference amplifier, and from there to a threshold detector 26. The threshold detector 26 has built-in a threshold or several thresholds with which the incoming voltage is compared. The threshold detector 26 delivers a binary information about the magnitude of each of the voltages $V_i$, $V_{i+1}$... These binary informations can be stored in memory cells of a memory 28. These informations represent the fingerprint. The memory 28 may be, for instance, a charge coupled device (CCD array). Such a charge coupled device is commercially available. If desired, the information stored in the memory 28 can be read out. It can also be displayed on a display device, such as a screen, printed out, or plotted on a chart.

Figure 8:
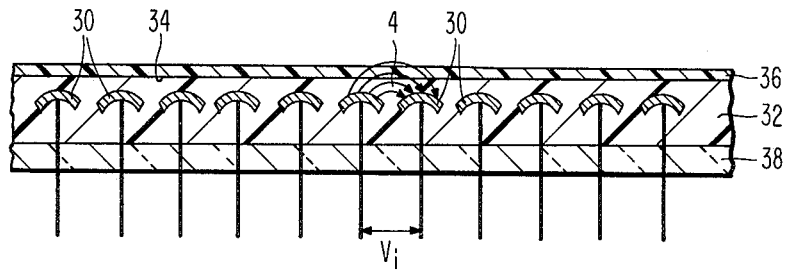
FIG. 8 is a fingerprint sensor having a large number of V-shaped electrodes, wherein two electrodes next to each other form a capacitor.
Figure 9:
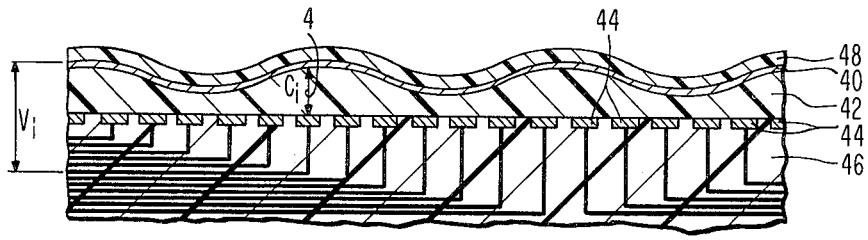
FIG. 9 is another fingerprint sensor having a large number of plane electrodes and a flexible electrode opposite to the plane electrodes.

FIGS. 8 and 9 illustrate embodiments of the mechanical part of a capacitive fingerprint sensor. Such sensors are easy to manufacture, especially if IC development techniques are employed.

According to FIG. 8, many V-shaped or curved metalic electrodes or plates 30 are provided in a sensing member 32. These metalic electrodes 30 are arranged in a plane close to the surface 34 of the sensing member 32. They are arranged such that the other part of the V is directed to the surface 34. The sensing member 32 is an electric insulator. The sensing surface is covered by a protective film 36 which also is an insulator.

Two V-shaped plates which are arranged next to each other form a capacitor. One of these capacitors is again denoted by the reference numeral 4. The voltage $V_i$ of each of these capacitors 4 can be measured since connection lines extend downward through a lower surface of the sensing member 32. The member 32 may be supported by a plate 38 made of a rigid material.

As soon as a finger will touch the surface of the protective film 36, the V-shaped plates 30, which are resilient will be deformed, thereby changing the capacitance of the capacitors 4. The distribution of the voltages $V_i$ of these capacitors 4 can be picked up and processed by multiplexing techniques.

It has to be noted that in the embodiment of FIG. 8 a change of the dielectric constant, due to an approach of the human finger, will also result in a change of the capacitance and voltage distribution.

The embodiment of FIG. 9 presumes a fixed dielectric constant. This embodiment is based on changes of the distance d between the electrodes of the individual capacitors 4.

In FIG. 9, a sensing member is formed by a flexible electrode 40, a flexible insulator 42, and a large number of flat metal plates 44 which are carried by a support member 46 of rigid structure. The metal plates 44 are all arranged in one plane which is parallel to the surface of the support member 46. The flexible electrode 40 may be covered by a flexible membrane or protecting coat 48 which is an electric insulator.

As can be seen in FIG. 9, the surface of the flexible membrane 48 becomes wavy under the influence of the ridges and valleys of a finger (not shown). The flexible electrode 40 follows also the ridge/valley pattern of the finger. The individual plates 44 form capacitors with the flexible electrode 40, whereby the insulator 42 represents the dielectric material within these capacitors. One capacitor 4 is illustrated to have the capacitance $C_i$ and the voltage $V_i$. Connection lines lead from each plate 44 to one side of the fingerprint sensor where they are connected to a reading circuitry (not shown in FIG. 9). As can be seen, the distance between the capacitor electrodes 40 and 44, respectively, varies from capacitor to capacitor in accordance with the pattern created on the surface of the sensor. Due to the change of distance, the capacitance and the voltge of each capacitor will vary. The voltage distribution can again be measured and processed by means of multiplexor techniques.

While the form of the fingerprint sensor herein described constitutes preferred embodiments of the invention, it is to be understood that the invention is not limited to these precise forms of assembly, and that a variety of changes may be made therein without departing from the scope of the invention.

What is claimed is:

1. A fingerprint sensor comprising in combination:
(a) a sensing member having a sensing surface for pressing a finger thereto;
(b) sensing means for sensing the ridges and valleys of the skin of said finger, said sensing means containing a multitude of capacitors located in said sensing member, the size of said capacitors being less than the size of said valleys; and
(c) said sensing member containing a multitude of metal plates, each forming a first electrode of said multitude of capacitors, whereby the capacitances of respective ones of said capacitors are locally changed in accordance with said ridges and valleys when said finger is pressed against said surface.

2. The fingerprint sensor according to claim 1, wherein said sensing member is an electric isolator, and wherein said metal plates are V-shaped and arranged below said sensing surface, each metal plate next to a plate forming a second electrode of said multitude of capacitors.

3. The fingerprint sensor according to claim 1, wherein said sensing member is formed by a flexible electrode, wherein said metal plates are arranged in a plane, and wherein a flexible electric isolator is located between said plane of metal plates and said flexible electrode.

4. The fingerprint sensor according to claim 1, wherein said sensing surface is covered by a protecting coat.

* * * * *